| United States Patent [19] | | [11] | 4,202,993 |
|---|---|---|---|
| Takekoshi | | [45] | May 13, 1980 |

[54] METHOD FOR MAKING SUBSTANTIALLY ANHYDROUS ALKALI METAL BISPHENOL SALTS

[75] Inventor: Tohru Takekoshi, Scotia, N.Y.

[73] Assignee: General Electric Company, Schenectady, N.Y.

[21] Appl. No.: 37,440

[22] Filed: May 9, 1979

[51] Int. Cl.$^2$ .............................................. C07C 39/16
[52] U.S. Cl. ..................................... 568/723; 528/126
[58] Field of Search ............................... 568/724, 723

[56] References Cited

U.S. PATENT DOCUMENTS

| 2,781,403 | 2/1957 | Kane et al. | 568/723 |
|---|---|---|---|
| 2,858,342 | 10/1958 | Bender et al. | 568/723 |
| 3,852,242 | 12/1974 | White | 528/28 |
| 3,960,968 | 6/1976 | Vernaleken et al. | 568/723 |
| 4,108,837 | 8/1978 | Johnson et al. | 528/126 |

OTHER PUBLICATIONS

Johnson et al., "Journal of Polymer Science", Part A-1, vol. 5, 2375-2398 (1967).
Schnell et al., "Angewandte Chemie", international edition, 2, 373 (1963).
Corson et al., "Journal of Organic Chemistry", 23, 544 (1958).

*Primary Examiner*—Joseph E. Evans
*Attorney, Agent, or Firm*—William A. Teoli; James C. Davis, Jr.

[57] ABSTRACT

A method is provided for making substantially pure anhydrous sodium salts of aromatic bisphenols, such as the disodium salt of 2,2-bis(p-hydroxyphenyl)propane. Rapid separation of water from a sodium salt of an aromatic bisphenol hydrate, or as an aqueous mixture having stoichiometric quantities of sodium hydroxide and bisphenol has been found to provide substantially pure anhydrous bisphenol alkali metal salts useful as intermediates for making polyetherimides.

5 Claims, No Drawings

METHOD FOR MAKING SUBSTANTIALLY ANHYDROUS ALKALI METAL BISPHENOL SALTS

CROSS REFERENCE TO RELATED APPLICATIONS

Reference is made to the copending application Ser. No. 037,441 of Frank J. Williams, III, for Method of Making Aromatic Ether Imides, and copending application Ser. No. 037,442 of Frank J. Williams, III et al, for Method for Making Alkali Metal Bisphenoxide Salts and Bisimides Derived Therefrom, both applications being filed concurrently herewith and assigned to the same assignee as the present invention.

BACKGROUND OF THE INVENTION

As taught in British Pat. No. 890,432, bisphenols are readily decomposed when heated, and alkalis readily catalyze bisphenol decomposition. Prior to the present invention, therefore, the production of substantially anhydrous alkali metal diphenoxide salts of the formula,

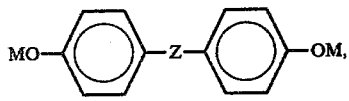

(1)

involving direct contact between alkali metal ion and bisphenol often required carefully controlled and multi-step procedures. As used hereinafter, the term "substantially anhydrous" signifies the bisphenol salt has less than 1% by weight of water based on the weight of bisphenol salt as determined with Karl Fischer reagent, where M is an alkali metal ion and Z is a divalent organic radical defined more particularly below. For example, White, U.S. Pat. No. 3,852,242, is based on the initial formation of an alkali metal alkoxide which is thereafter reacted with a bisphenol in the presence of a hydrocarbon solvent. The excess hydrocarbon is stripped from the mixture and the resulting bisphenol salt dried under reduced pressure at 100° C. for one hour.

The present invention is based on the discovery that bisphenols neutralized with a substantially stoichiometric equivalent of an alkali metal hydroxide are very stable at elevated temperatures and that substantially anhydrous diphenoxide salts of formula (1) can be made more directly and faster and recovered as a substantially pure and anhydrous powder by heating at temperatures up to 350° C., a hydrate of the diphenoxide salt, such as disodium bisphenol-A hexahydrate, or an aqueous mixture of bisphenol and alkali metal hydroxide, for example, bisphenol-A and sodium hydroxide, where the bisphenol and the alkali metal hydroxide are present in the aqueous mixture in substantially stoichiometric proportions.

STATEMENT OF THE INVENTION

There is provided by the present invention a method which comprises, (1) effecting the flash evaporation of water at a temperature in the range of up to 350° C. from a hydrate of a bisphenol salt selected from the class consisting of (A) a material substantially free of physically associated water consisting essentially of hydrate of bisphenol alkali metal salt, and (B) an aqueous solution or slurry resulting from the neutralization of bisphenol with a stoichiometric equivalent of an alkali metal hydroxide in the presence of water, (2) recovering the substantially anhydrous residue from the mixture of (1).

Alkali metals included by M of formula (1) are, for example, sodium, potassium, lithium, etc. Radicals included by Z of formula (1) are, for example

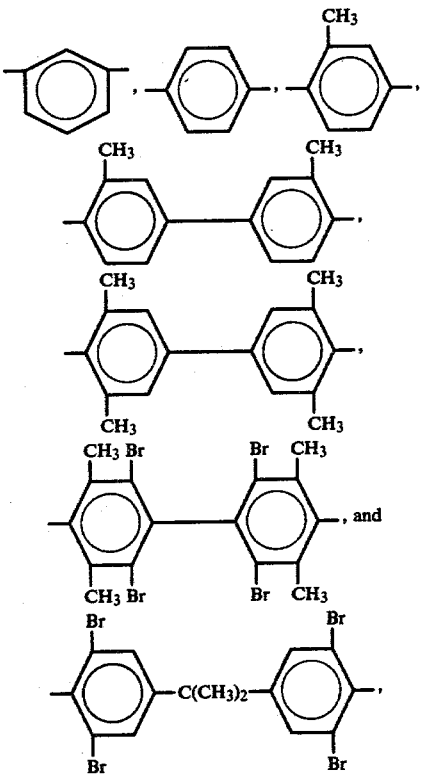

and divalent organic radicals of the general formula

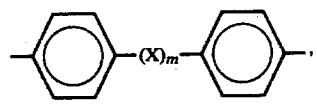

where X is a member selected from the class consisting of divalent radicals of the formulas, $-C_yH_{2y}-$,

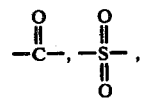

$-O-$ and $-S-$, where m is 0 or 1, and y is a whole number from 1 to 5.

Included by the bisphenols which can be converted to alkali metal salts in accordance with the practice of the invention are, for example, 2,2-bis(2-hydroxyphenyl)propane;
2,4'-dihydroxydiphenylmethane;
bis(2-hydroxyphenyl)methane;

2,2-bis(4-hydroxyphenyl)propane, hereinafter identified as "bisphenol-A" or "BPA";
2(4-hydroxyphenyl)-2(3'-hydroxyphenyl)propane;
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'dihydroxy-3,3',5,5'-tetramethylbiphenyl;
2,4'-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihydrozybenxophenone; and
4,4'-dihydroxydiphenyl ether.

As shown in copending application Ser. No. 037,441 of Frank J. Williams, filed concurrently herewith, the bisphenoxide salts of the present invention can be used to make aromatic ether bisimide, or polyetherimides based on the nature of the nitro-, or halo-phthalimide used. For example, the bisphenoxide salts of formula (1) can be used in combination with bis(nitrophthalimide) in the Method for Making Polyetherimides, U.S. Pat. No. 3,852,242, assigned to the same assignee as the present invention. The bisphenoxide salts made by the method of the present invention also can be used to make polyethersulfones, polycarbonates, polyesters and epoxy derivatives.

In the practice of the invention, a hydrated bisphenol salt, either in the form of a compound, or an aqueous mixture is contacted to a heated surface to effect the separation of water, the production of a substantially anhydrous powder therefrom and the recovery of the resulting powder.

Preferably, the temperature of the surface is sufficiently high, such as up to about 350° C. to provide flash evaporation of water from the hydrate of the bisphenol salt which can exist and isolated and decomposed as a chemical compound, or as an in situ formed material dissolved in water requiring the physical separation of water.

Evaporation of water from the hydrated bisphenol salt can be effected by direct contact with a hot surface, such as a hot plate, drum drier, by use of spray drying, fluidized bed, etc.

Recovery of the powdered bisphenol salt can be readily achieved as it is in the form of a substantially anhydrous dry powder. The bisphenol salt can be stored for an indefinite period of time under sealed conditions.

In order that those skilled in the art will be better able to practice the invention, the following examples are given by way of illustration and not by way of limitation. All parts are by weight.

EXAMPLE 1

A mixture of 2.020 parts of bisphenol-A, 1.407 part of a 50.3% aqueous sodium hydroxide solution and 1.93 part of water was briefly heated to a boil. The resulting fluid slurry of the bisphenol-A disodium salt was spread over a nickle coated brass sheet on a hot plate which was inside of a dry box and which was preheated at 300° to 320° C. Evaporation of the water was instantaneous, resulting in a white powdery solid. Based on method of preparation, the powdery solid was the disodium salt of bisphenol-A. After a total heating time of 60 seconds, the bisphenol-A salt was collected. Proton NMR spectrum in $D_2O$ solution indicated that the product was free of decomposition product. In addition, the IR spectrum of the bisphenol-A salt indicated that the product was completely anhydrous.

A dispersion of 1.4 part of the anhydrous bisphenol-A disodium salt was made with 15 parts of dimethylsulfoxide. There was added to the dispersion 2.120 parts of N-methyl-4-nitrophthalimide and the resulting mixture was stirred at 75° C. under nitrogen for one hour. The reaction mixture was cooled and poured into water. There was obtained a white precipitate which was filtered, washed with water and dried. Based on method of preparation, the product was 4,4'-bis(N-methylphthalimide-4-oxy)-2,2-diphenylpropane. The yield of product was 97%.

EXAMPLE 2

A slurry of the disodium salt of bisphenol-A was prepared in accordance with the procedure of Example 1. The aqueous slurry is then fed onto a heated calender while being swept with an inert gas which is directed across the disodium bisphenol-A salt as it is conveyed on a heated metal belt and allowed to spill over into a collector. There is obtained a substantially anhydrous disodium salt of bisphenol-A having less than 0.5% by weight of water based on the use of Karl Fischer reagent.

Although the above examples are directed to only a few of the very many variables of the method of the present invention, it should be understood that the present invention is directed to a much broader process for making alkali metal bisphenol salts as described in the specification preceding these examples.

What I claim as new and desire to secure by Letters Patent of the United States is:

1. A method which comprises,
   (1) effecting the flash evaporation of water at a temperature in the range of up to 350° C. from a hydrate of a bisphenol salt selected from the class consisting of
      (A) a material substantially free of physically associated water consisting essentially of hydrate of bisphenol alkali metal salt, and
      (B) an aqueous solution or slurry resulting from the neutralization of bisphenol with a stoichiometric equivalent of an alkali metal hydroxide in the presence of water,
   (2) recovering substantially anhydrous residue from the mixture of (1).
2. A method in accordance with claim 1, where the bisphenol is bisphenol-A.
3. A method in accordance with claim 1, where the alkali metal hydroxide is sodium hydroxide.
4. A method in accordance with claim 1, where the flash evaporation is achieved by spray drying.
5. A method in accordance with claim 1, where the flash evaporation is achieved by drum drying.

* * * * *

UNITED STATES PATENT AND TRADEMARK OFFICE
CERTIFICATE OF CORRECTION

PATENT NO. : 4,202,993
DATED : May 13, 1980
INVENTOR(S) : Tohru Takekoshi

It is certified that error appears in the above–identified patent and that said Letters Patent are hereby corrected as shown below:

Column 1, line 26, cancel

"  "

and substitute the following formula:

-- MO-Z-OM --

Signed and Sealed this

Nineteenth Day of August 1980

[SEAL]

*Attest:*

*Attesting Officer*

SIDNEY A. DIAMOND

*Commissioner of Patents and Trademarks*